(12) United States Patent
Otte

(10) Patent No.: US 6,468,305 B1
(45) Date of Patent: Oct. 22, 2002

(54) TWO PIECE VALVE

(75) Inventor: John F. Otte, St. Anthony Village, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/571,801

(22) Filed: May 16, 2000

(51) Int. Cl.[7] .................................................. A61F 2/06
(52) U.S. Cl. ........................................ 623/2.4; 623/2.39
(58) Field of Search ................................. 623/2.1, 2.39, 623/2.4, 2.38, 2.41, 2.11; 411/259; 215/274

(56) References Cited

U.S. PATENT DOCUMENTS

| | | | |
|---|---|---|---|
| 3,143,742 A | 8/1964 | Cromie .............................. 3/1 |
| 3,503,079 A | 3/1970 | Smith ................................ 3/1 |
| 3,546,710 A | 12/1970 | Shumakov et al. ................ 3/1 |
| 3,574,865 A | 4/1971 | Hamaker ........................... 3/1 |
| 3,587,115 A | 6/1971 | Shiley ................................ 3/1 |
| 3,686,740 A | 8/1972 | Shiley .......................... 29/439 |
| 3,996,623 A | 12/1976 | Kaster ............................. 3/1.5 |
| 3,997,923 A | 12/1976 | Possis ............................. 3/1.5 |
| 4,078,268 A | 3/1978 | Possis ............................. 3/1.5 |
| 4,364,126 A | 12/1982 | Rosen et al. .................... 3/1.5 |
| 4,506,394 A | 3/1985 | Bedard ............................ 3/1.5 |
| 4,612,011 A | 9/1986 | Kautzky ......................... 623/2 |
| 4,680,031 A | 7/1987 | Alonso ........................... 623/2 |
| 4,705,516 A | 11/1987 | Barone et al. ................. 623/2 |
| 4,790,843 A * | 12/1988 | Carpentier et al. ............ 623/2 |
| 4,892,541 A | 1/1990 | Alonso ........................... 623/2 |
| 5,032,128 A | 7/1991 | Alonso ........................... 623/2 |
| 5,035,709 A | 7/1991 | Wieting et al. ................. 623/2 |
| 5,071,431 A | 12/1991 | Sauter et al. ................... 623/2 |
| 5,163,954 A | 11/1992 | Curcio et al. .................. 623/2 |
| 5,354,330 A | 10/1994 | Hanson et al. ................. 623/2 |
| 5,397,346 A | 3/1995 | Walker et al. ................. 623/2 |
| 5,562,729 A | 10/1996 | Purdy et al. .................... 623/2 |
| 5,607,470 A | 3/1997 | Milo .............................. 623/2 |
| 5,716,370 A | 2/1998 | Williamson, IV et al. .. 606/153 |
| 5,766,240 A * | 6/1998 | Johnson ......................... 623/2 |
| 5,776,188 A | 7/1998 | Shepherd et al. .............. 623/2 |
| 6,113,632 A * | 9/2000 | Reif ............................. 623/2.4 |
| 6,143,025 A * | 11/2000 | Stobie ....................... 623/2.39 |

FOREIGN PATENT DOCUMENTS

| | | |
|---|---|---|
| CH | 307728 | 8/1985 |
| DE | 1180087 | 10/1964 |
| DE | 35 07 109 A1 | 9/1986 |
| EP | 0 119 357 A1 | 9/1984 |
| EP | 0 544102 A1 | 6/1993 |
| FR | 1 386 811 | 12/1964 |
| GB | 1 600 506 | 10/1981 |
| SU | 1 222 264 A | 8/1983 |
| WO | WO 87/05489 | 9/1987 |
| WO | WO 91/14408 | 10/1991 |
| WO | WO 96/03925 | 2/1996 |
| WO | WO 96/12452 | 5/1996 |
| WO | WO 97/09948 | 3/1997 |
| WO | WO 97/30659 | 8/1997 |

* cited by examiner

*Primary Examiner*—Paul B. Prebilic
*Assistant Examiner*—William H Matthews
(74) *Attorney, Agent, or Firm*—Westman, Champlin & Kelly

(57) ABSTRACT

A prosthetic heart valve for implantation in a heart includes an outer orifice ring and an inner orifice ring having an occluding mechanism carried therein. A ring coupling mechanism having helical threads is adapted to couple the outer orifice ring to the inner orifice ring after the outer orifice ring has been coupled to the tissue annulus. The coupling mechanism comprises a first helical thread on an outer diameter of the inner ring and a second helical thread on an inner diameter of the outer ring. At least one of the diameters includes a retaining ridge configured to define an unthreaded region between the retaining ridge and the respective thread. When a helical thread is positioned in the unthreaded region, the inner ring is rotatable in the outer ring with substantially no movement in an axial direction of the valve.

13 Claims, 5 Drawing Sheets

TWO PIECE VALVE

FIELD OF THE INVENTION

The present invention relates to mechanical heart valve prostheses. More specifically, the invention relates to a mechanism for attaching and implanting heart valve prostheses.

BACKGROUND OF THE INVENTION

Implantable prosthetic heart valves are used for replacement of defective valves in hearts of patients. There are two general types of hearts valves, mechanical and bioprosthetic. One method of implanting a valve employs a sewing ring or suture cuff which is attached to and extends around the outer circumference of the valve orifice. The sewing cuff is made of a biocompatible fabric suitable for allowing a needle and suture to pass therethrough. The valve is typically sutured to a tissue annulus after the surgeon removes the native valve from the patient's heart. The sutures are tied snugly, thereby securing the valve to the heart.

Attaching the suture cuff to the tissue annulus is time consuming, and requires a patient to be on cardiopulmonary bypass for an extended period.

One technique for attaching a prosthetic heart valve to the heart tissue is shown in U.S. Pat. No. 4,705,516 in which an outer orifice ring is sutured to the tissue annulus and an inner orifice ring is then screwed into the outer orifice ring. However, the rings are not locked together and may become unscrewed after extended use.

SUMMARY OF THE INVENTION

A prosthetic heart valve for implantation in a heart is provided which includes an outer orifice ring, an attachment mechanism on the outer orifice ring adapted to couple the outer orifice ring to a tissue annulus of the heart, an inner orifice ring having an occluding mechanism carried therein, and a ring coupling mechanism adapted to couple. the outer orifice ring to the inner orifice ring after the outer orifice ring has been coupled to the tissue annulus. The coupling mechanism includes a first helical thread on an outer diameter of the inner ring and a second helical thread on an inner diameter of the outer ring. At least one of the diameters includes a retaining ridge configured to define an unthreaded region between the retaining ridge and the respective thread. When a helical thread is positioned in the unthreaded region, the inner ring is rotatable in the outer ring with substantially no movement in an axial direction of the valve.

DETAILED DESCRIPTION OF THE PREFERRED EMBODIMENTS

The present invention relates to heart valve prostheses including mechanical, tissue (such as stented tissue) and polymer heart valves. The present invention provides a heart valve prosthesis having an inner orifice ring and an outer orifice ring. The inner orifice ring includes a helical thread on its outer diameter and the outer orifice ring includes a helical thread on its inner diameter. The two threads are configured to mate such that the inner and outer rings can be screwed together by rotating one of the rings relative to the other ring. However, at least one of a the rings is provided with an unthreaded region between the thread and a retaining ridge. Once the rings-have been positioned such that one of the threads is in this unthreaded region, the inner ring can be rotated without axial movement therebetween. In this position, the threads on the outer orifice ring and the threads on the inner orifice ring are not engaged with one another. Further, the retaining ridge serves to axially retain the two rings.

Figure 1:
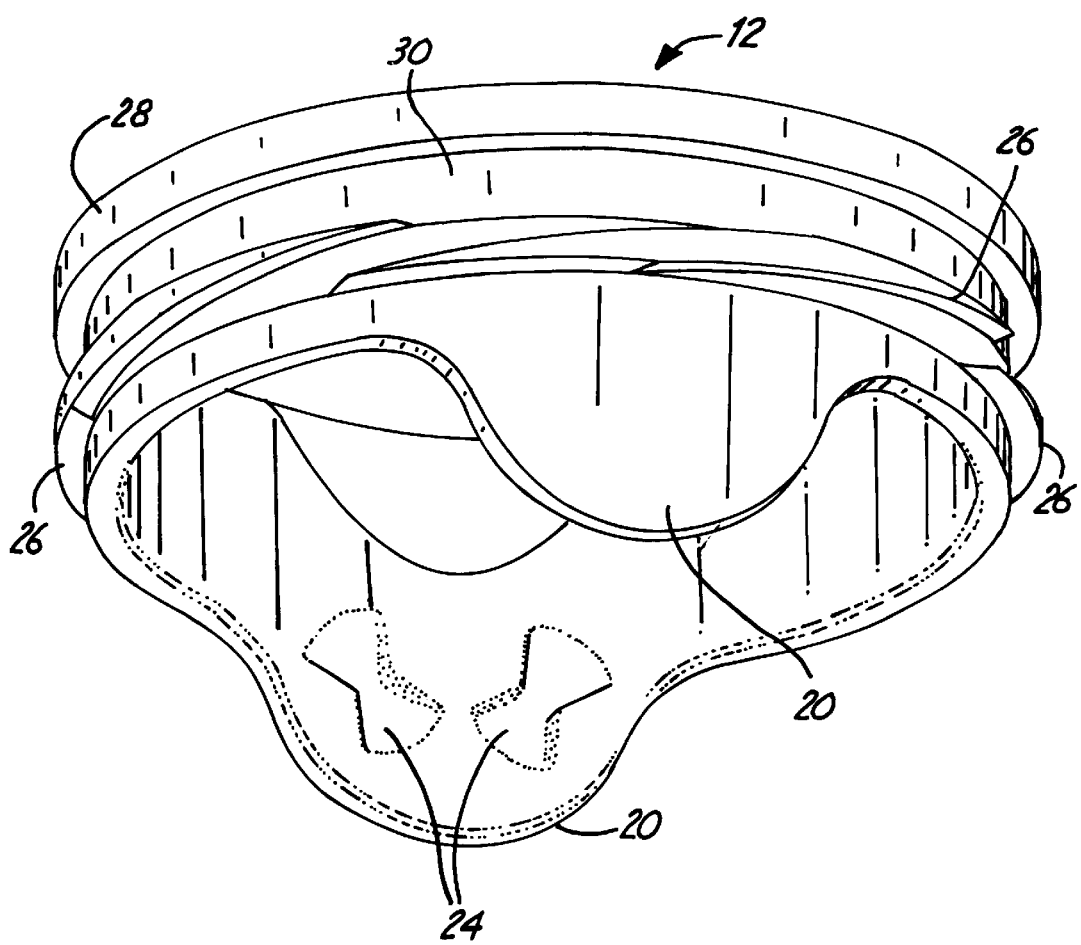
FIG. 1 is a perspective view of an inner mechanical valve orifice ring of the present invention.

FIG. 1 is a perspective view of an inner mechanical heart valve orifice ring 12 in accordance with the present invention. Those skilled in the art will recognize that the present invention can be used with hearts valves for mitral or aortic implantation. Inner orifice ring includes pivot guards 20 having pivot recesses 24 formed therein on each pivot guard. Helical threads 26 extend around an outer diameter of inner ring 12. A retaining ridge 28 also extends around the outer diameter of inner ring 12. Ridge 28 is spaced apart from the helical threads 26 to form an unthreaded region 30 therebetween. Ridge 28 can be positioned as desired for a particular configuration-and is not limited to the specific example set forth herein.

Figure 2:
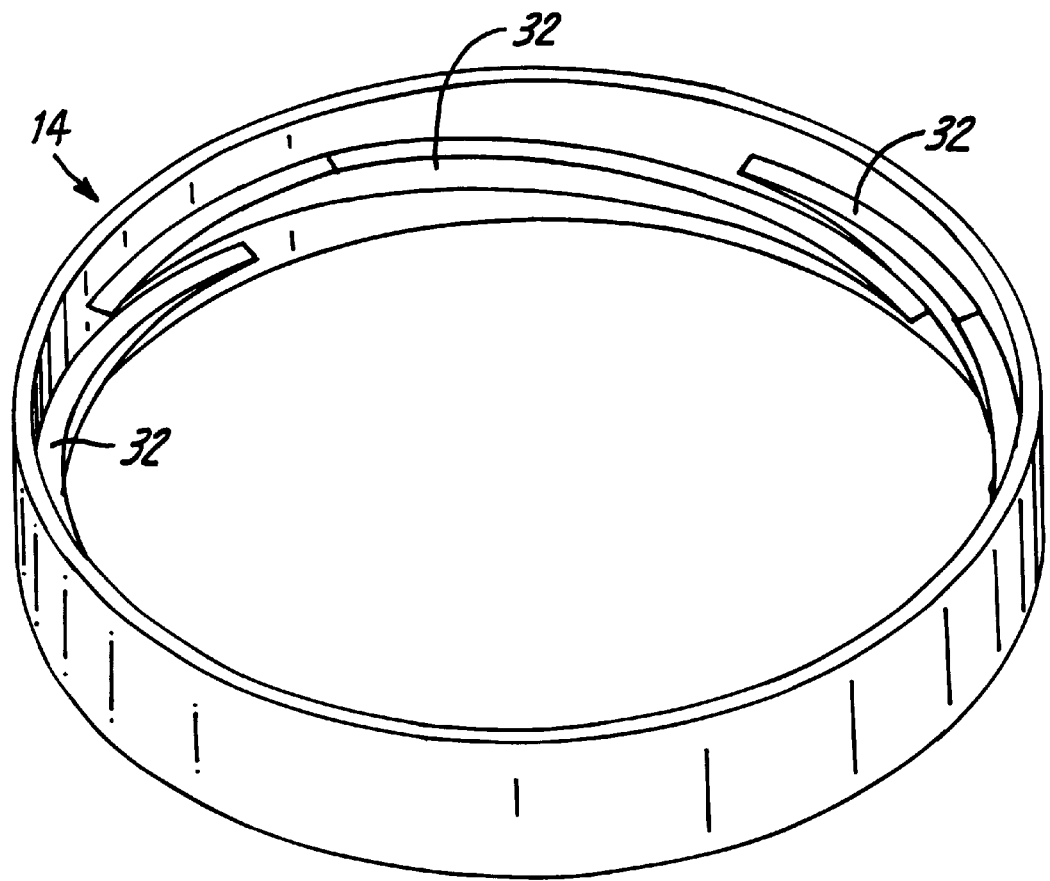
FIG. 2 is a perspective view of an outer orifice ring of the present invention.

FIG. 2 is a perspective view of outer orifice-ring 14 which includes the helical threads 32 formed around its inner diameter. Threads 32 are configured to mate with threads of an annulus ring of the invention such as threads 26 of ring 12 of FIG. 1. Outer orifice ring 14 is mated with inner orifice ring 12 by placing the two rings 12, 14 together and providing a relative rotation. This causes the two rings to be screwed together. Once threads 32 are positioned in unthreaded region 30, threads 32 will be retained between threads 26 and retaining ridge 28 of inner orifice ring 12. In this position, ring 12 can be rotated in either direction and into the proper orientation relative to ring 14 and the tissue annulus without any axial movement due to the interaction between threads 26 and threads 32. However, ring 12 can be separated from ring 14 through the application of an axial force while providing relative rotation, for example, for a subsequent operation to replace a tissue valve. This causes threads 26 to engage threads 32. This configuration is similar to a child-resistant cap. Note that ridge 28 can be positioned on either inner ring 12 or outer ring 14.

Figure 3A:
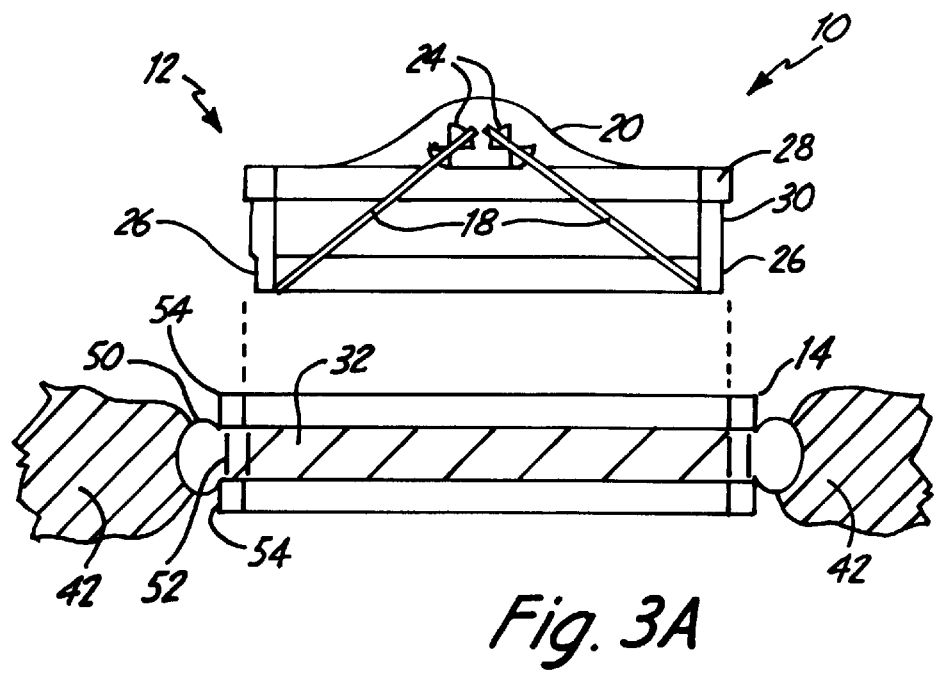
FIGS. 3A, 3B and 3C are exploded cross-sectional views of example mechanical prosthetic heart valves using the inner and outer orifice rings of the invention.
Figure 3B:
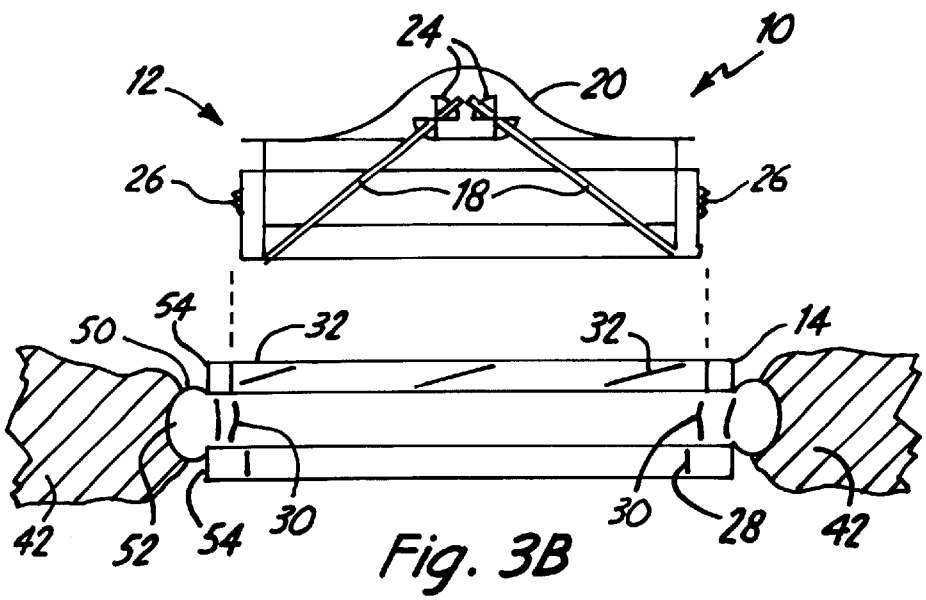
Figure 3C:
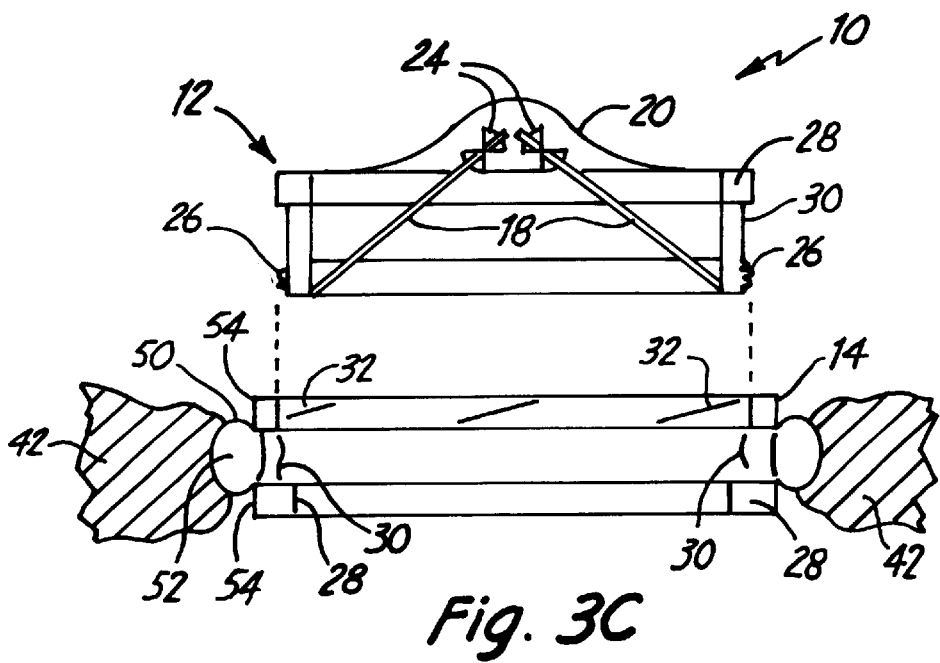

FIG. 3A is an exploded perspective view showing mechanical heart valve prosthesis 10 which includes an inner orifice ring 12 and outer orifice ring 14. In one embodiment, ridge. 28 is. provided on the inner ring 12. FIG. 3A shows outer orifice ring 14 coupled to a tissue annulus 42 through a sewing cuff 50. Sewing cuff 50 is held in a recess 52 located between the ridges 54. Suture cuff 50 is provided as one example of an attachment mechanism for attaching outer orifice ring 14 to tissue annulus 42. Any type of attachment mechanism as known or contemplated in the art can be utilized, such as helical screws. In FIG. 3A, inner orifice ring 12 is illustrated with an occluding mechanism specifically illustrated as occluders 18 which rotate in pivot recesses 24. Other occluding or pivot mechanisms can also be used. FIGS. 3B and 3C show other example embodiments. In FIG. 3B, threads 26 are positioned near the middle of ring 12 and ridge 28 is carried on ring 14. In FIG. 3C, both rings 12 and 14 carry ridges 28.

Figure 4:
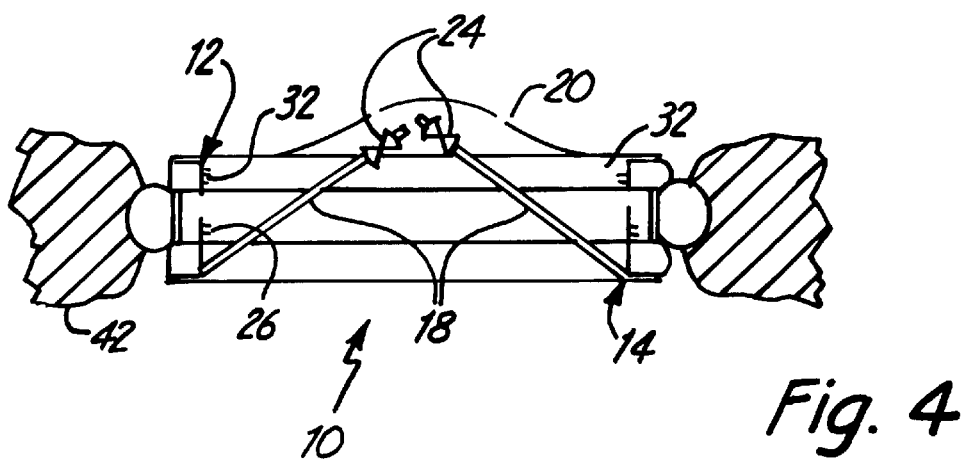
FIG. 4 is a side cross sectional view of the prosthetic heart valve of FIG. 3A.

FIG. 4 shows heart valve prosthesis 10 in which inner orifice ring 12 has been positioned in outer orifice ring 14. This positioning is achieved by rotating ring 12 relative to ring 14 such that threads 26 engage threads 32. As this rotation continues, ring 12 moves in an axial direction relative to ring 14 until threads 26 and 32 reach the respective unthreaded region 30. In this position, further rotation of rings 12 and 14 does not cause any further axial movement. Further, ring 12 will be axially retained in place due to retaining ridge 28 and the interaction between threads 26 and 32.

In one preferred embodiment, a surgeon initially implants outer ring 14 as illustrated in FIG. 3A. Because the inner ring and occluding mechanism of prosthesis 10 is not present during implantation, the invention provides improved visibility of subvalvular structures, the implantation is easier, and can be performed faster and with improved accuracy. Following implantation of ring 14, ring 12 can be rotated into the preferred orientation as illustrated in FIG. 4. Preferably, there is a frictional fit between ring 12 and ring 14 when positioned as illustrated in FIG. 4. This allows the surgeon to rotate inner ring 12 such that the occluding mechanism can have the desired orientation. The frictional fit between rings 12 and 14 will maintain this orientation.

Rings 12 and 14 are preferably fabricated of a biocompatible material. Examples of such material include pyrolytic carbon, polyetheretherketone (PEEK), titanium, polyurethane, or other materials including polymers and metals that are known in the art. The particular orientation and configuration of the threads on the inner and outer rings, the retaining ridge and the unthreaded regions can be adjusted as desired. The illustrations set forth herein simply provide one example orientation and configuration. Other types of occluding mechanisms or attachment mechanisms can also be employed with the present invention.

Figure 5:
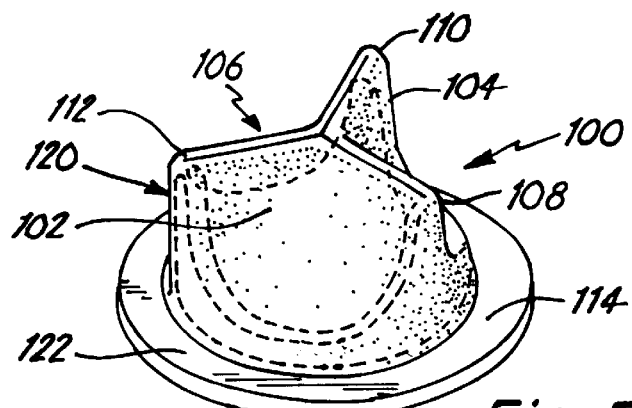
FIG. 5 is a perspective view of a polymer heart valve in accordance with one embodiment.

The present invention can also be used with flexible or tissue heart valves. For example, FIG. 5 is a perspective view of a heart valve prosthesis with flexible polymer leaflets or occluders 102, 104 and 106 joined at commissures 108, 110, and 112. This configuration forms an inner orifice ring 120 in accordance with the invention. An outer ring 122 is provided and can be implanted prior to coupling to inner ring 120, as discussed above. Rings 120 and 122 include threads and unthreaded regions and can be coupled together, as discussed above.

Figure 6:
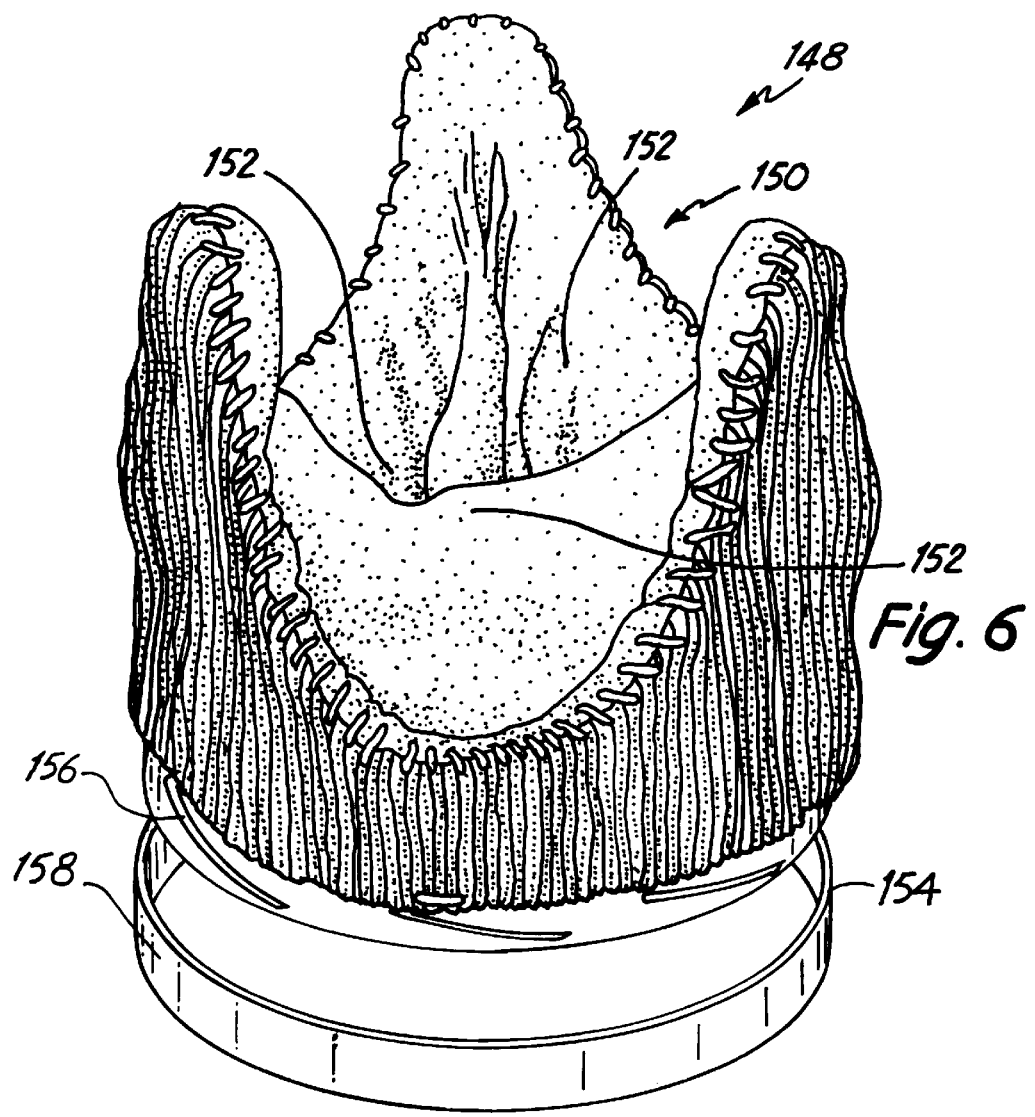
FIG. 6 is a perspective view of a tissue heart valve in accordance with one embodiment.

FIG. 6 is a perspective view of a bioprosthetic tissue heart valve 148 in accordance with another example of the present invention. Valve 148 includes leaflets 152 carried on an inner orifice ring 150 of the invention. An outer orifice ring 154 includes threads 158 on an inner diameter that are configured to mate with threads 156 on an outer diameter of ring 150. This coupling is in accordance with the invention as set forth above.

Although the present invention has been described with reference to preferred embodiments, workers skilled in the art will recognize that changes may be made in form and detail without departing from the spirit and scope of the invention.

What is claimed is:

1. A prosthetic heart valve for implantation in a heart, comprising:

an outer orifice ring;

a tissue attachment mechanism on the outer orifice ring adapted to couple the outer orifice ring to a tissue annulus of the heart;

an inner orifice ring having an occluding mechanism carried therein; and a ring coupling mechanism adapted to couple the outer orifice ring to the inner orifice ring after the outer orifice ring has been coupled to the tissue annulus, the coupling mechanism comprising a first helical thread on an outer diameter of the inner ring and a second helical thread on an inner diameter of the outer ring, at least one of the diameters including a retaining ridge configured to define an unthreaded region between the retaining ridge and the respective thread, wherein when a helical thread of the other ring is positioned in the unthreaded region, the inner ring is rotatable in the outer ring with substantially no movement in an axial direction of the valve.

2. The prosthetic heart valve of claim 1 wherein the occluding mechanism comprises a pair of moveable leaflets pivotably carried in a lumen through the inner orifice ring, the leaflets being moveable between an open position allowing blood flow therethrough and a closed position blocking blood flow therethrough.

3. The prosthetic heart valve of claim 1 wherein the tissue attachment mechanism comprises a suture cuff.

4. The prosthetic heart valve of claim 1 wherein the ring coupling mechanism comprises a plurality of helical threads on the inner orifice ring.

5. The prosthetic heart valve of claim 1 wherein the ring coupling mechanism comprises a plurality of helical threads on the outer orifice ring.

6. The prosthetic heart valve of claim 1 wherein the retaining ridge is integral with the inner orifice. ring.

7. The prosthetic heart valve of claim 1 wherein the retaining ridge is integral with the outer orifice ring.

8. The prosthetic heart valve of claim 1 wherein a frictional fit between an outer diameter of the inner orifice ring and an inner diameter of the outer orifice ring is sufficient to prevent relative rotation of the rings during normal operation of the prosthetic heart valve.

9. The prosthetic heart valve of claim 1 wherein the occluding mechanism comprises tissue leaflets.

10. The prosthetic heart valve of claim 1 wherein the occluding mechanism comprises polymer leaflets.

11. The prosthetic heart valve of claim 1 wherein the unthreaded region is located on the inner ring.

12. The prosthetic heart valve of claim 1 wherein the unthreaded region is located on the outer ring.

13. The prosthetic heart valve of claim 1 wherein both relative axial and rotational forces are required to separate the ring.

* * * * *